United States Patent [19]

Obata et al.

[11] Patent Number: 5,663,047

[45] Date of Patent: Sep. 2, 1997

[54] HLA-DR ANTIGEN GENE AND ITS NUCLEOTIDE SEQUENCE AND ITS USE

[75] Inventors: Fumiya Obata, Sagamihara; Noboru Kashiwagi, Tokyo, both of Japan

[73] Assignees: Mitsui Petrochemical Industries, Ltd.; The Kitasato Institute, both of Tokyo, Japan

[21] Appl. No.: 264,250

[22] Filed: Jun. 22, 1994

Related U.S. Application Data

[63] Continuation of Ser. No. 745,444, Aug. 15, 1991, abandoned.

[30] Foreign Application Priority Data

Aug. 20, 1990 [JP] Japan .................. 2-217209

[51] Int. Cl.$^6$ .................. C12Q 1/68; C07H 21/04
[52] U.S. Cl. .................. 435/6; 536/24.31
[58] Field of Search .................. 435/6; 536/24.31

[56] References Cited

U.S. PATENT DOCUMENTS

| | | | |
|---|---|---|---|
| 4,683,202 | 7/1987 | Mullis | 435/91 |
| 4,835,098 | 5/1989 | Orr et al. | 435/6 |
| 4,847,201 | 7/1989 | Kaswasaki et al. | 435/69.5 |
| 4,917,999 | 4/1990 | Byng et al. | 435/6 |
| 4,956,281 | 9/1990 | Wallner et al. | 435/69.3 |
| 5,013,649 | 5/1991 | Wang et al. | 435/69.1 |
| 5,026,837 | 6/1991 | Litt et al. | 536/24.31 |

FOREIGN PATENT DOCUMENTS

WO8904875  6/1989  WIPO.

OTHER PUBLICATIONS

Obata et al. Oligonucleotide–genotyping as a method of detecting the HLA–DR2 (DRw15)–Dw2, –DR2 (DRw15)–Dw12, –DR4–Dw15, and –DR4–D "KT2" haplotypes in the Japanese population. Tissue Antigens vol. 33 550–558. 1989.

Scharf et al. Sequence analysis of the HLA–DRB and HLA–DQB loci from three Pemphigus vulgaris patients. Human Immunology vol. 22 61–69. 1988.

Tosi, et al., Biochemistry 26 8516–8524 (1987).
Scharf, et al. Human Immunology 22 61–69 (1988).
Deen and Sweet, Journal of Virology 57 422–432 (1986).
Cladaras, et al., Embo Journal 5 3495–3507 (1986).
Feghali et al., Journal of Cell Biology 108 1791–1797 (1989).
Gowki, Human Immunology, v. 24, 1989, 145–9.
Mariatis et al. Molecular Cloning–A Laboratory Manual, Second Edition, 1989, Cold Spring Harbor Bab Press, p.5.58.
Erlich, Gene Seq, Accession # N92642.
Immunogenetics, vol. 32, No. 2, 1990, pp. 96–103 Petersdorf, et al., "Unique Sequences for Two HLA–DRBI Genes Expressed on Distinct DRw6 Haplotypes".
Immunology, vol. 142, No. 5, pp. 1743–1747 Kao, et al., Mar. 15, 1989, "Molecular Analysis of the HLA Class II Genes in Two DRw6–Related Haplotypes, DRw13.".
Immunogenetics, 30:422–426, 1989, Abe, et al., "Two Distinct Subtypes of the HLA–DRw12 Haplotypes in the Japanese Population Detected by . . . . .".
Human Immunology, 27:269–284, 1990, Obata, et al. "Sequence Analysis and Oligonucleotide Genotypig of HLA–DR JX6", a DR blank Haplotype . . . .
Fumiya Obata, et al., Tissue Antigens, (1989), 33, 550–558.
Fumiya Obata, et al., Human Immunology, (1990), 27, 269–284.
Akio Abe, et al., Immunogenetics (1989), 30, 422–426.
Fumiya Obata, et al., Immunogenetics, (1990), 32, 313–32.

*Primary Examiner*—James Ketter
*Assistant Examiner*—John S. Brusca
*Attorney, Agent, or Firm*—Sherman and Shalloway

[57] ABSTRACT

We have found a novel subtype DRw14c and sequenced the nucleotide sequence thereof. DRw14 associated genes can be genetically typed at the DNA level using DRB1-14c sequence specific oligonucleotide probes such as F142 and F144 of the invention. The present invention overcomes the disadvantages of serological typing and provides a reagent that determines a type of a HLA-DR antigen. More specifically, the invention provides an oligonucleotide probe capable of identifying subtypes of a HLA-DR antigen precisely and a reagent containing the oligonucleotide probe. Furthermore, the invention provides a method of detecting a novel HLA-DR antigen.

11 Claims, 3 Drawing Sheets

FIG. 1

| FIG. 1A |
|---------|
| FIG. 1B |

FIG. 1A

NUCLEOTIDE SEQUENCE OF THE DRB1 – SECOND EXON OF
THE DRB1-14c ALLELE AND DEDUCED AMINO ACID SEQUENCE

```
                         20                   40                              60                          80
DRB1-14c        Primer-T TTC TTG GAG TAC TCT ACG TCT GAG TGT CAA TTC TTC AAT GGG ACG GAG CGG GTG CGG TTC CTG GAC
(NUCLEOTIDE              ─────────────F144────────────▶
SEQUENCE)
DRB1-14c                 Phe Leu Glu Tyr Ser Thr Ser Glu Cys Gln Phe Phe Asn Gly Thr Glu Arg Val Arg Phe Leu Asp
(AMINO ACID              7                    10                             20
SEQUENCE)
DRB1*1401       CACG---  --- --- --- --- --- --- --- --- --- --- --- -T- --- --- --- --- --- --- --- --- ---
(Dw 9)
(NUCLEOTIDE
SEQUENCE)
DRB1*1402       CACG---  --- --- --- --- --- --- --- --- --- --- --- -T- --- --- --- --- --- --- --- --- ---G
(Dw16)                                                                                            ◀──F52c
(NUCLEOTIDE
SEQUENCE)

100                          120                         140                        16
DRB1-14c        AGA TAC TTC CAT AAC CAG GAG GAG TTC GTG CGC TTC GAC AGC GAC GTG GGG TAC CGG GCG GTG ACG GAG CTG
(NUCLEOTIDE                                            ◀────F141────
SEQUENCE)
DRB1-14c        Arg Tyr Phe His Asn Gln Glu Glu Phe Val Arg Phe Asp Ser Asp Val Gly Tyr Arg Ala Val Thr Glu Leu
(AMINO ACID             30                              40                          50
SEQUENCE)
DRB1*1401       --- --- --- --- --- --- --- --- --- --- --- --- --- --- --- --- --- --- --- --- --- --- --- ---
(Dw 9)                                                 ────F141────▶
(NUCLEOTIDE
SEQUENCE)
DRB1*1402       --- --- --- --- --- --- --- --- --- --- --AA- --- --- --- --- --- --- --- --- --- --- --- ---
(Dw16)                  ─────────────────────▶
(NUCLEOTIDE
SEQUENCE)
```

FIG. 2

RESULTS OF TYPING USING OLIGONUCLEOTIDE PROBES

SSO probes

| Donor | DR | F6b | F141 | F144 | F142 | F143 | F46 | F52c | DRw14-related allele |
|---|---|---|---|---|---|---|---|---|---|
| 26F | w14,9 | ● | ● | ● | ● | | | | 14c |
| 36M | w14,w15 | ● | ● | ● | ● | | | | 14c |
| 38M | w14,4 | ● | ● | ● | ● | | ● | | 14c |
| KW | w14,9 | ● | ● | | | ● | | | 1401 |
| 24F | w14,w8 | ● | ● | | | ● | | | 1401 |
| 38F | w14,w11 | ● | ● | ˙ | | ● | | ˙ | 1401 |
| 59M | w14,9 | | | | | | ● | ● | 1402 |
| 75M | w14,w8 | | ˙ | | | | ● | ● | 1402 |

HLA-DR ANTIGEN GENE AND ITS NUCLEOTIDE SEQUENCE AND ITS USE

This application is a continuation of application Ser. No. 07/745,444, filed Aug. 15, 1991 which is now abandoned.

FIELD OF THE INVENTION

The present invention relates to a nucleotide sequence of a DR antigen, a human leucocyte antigen (HLA), an oligonucleotide probe for genetic typing of the DR antigen at the DNA level, a method of genetic typing of the DR antigen using the oligonucleotide probe, and a reagent used for DR typing.

BACKGROUND OF THE INVENTION

HLA typing plays important roles in analyzing histocompatibility for organ transplants and determining an individual's susceptibility to certain diseases. Kidney transplants are frequently performed in Japan and it has been reported that the organ transplantation from related donors (e.g. family member) gives better survival of transplanted organ than that from unrelated donors, even though the HLA matching between a recipient and an unrelated donor is maximized by serologic HLA typing. This fact suggests that there may be some HLA subtypes that are not identifiable by the conventional serologic typing, or the influences by other unknown genes closely linked to the HLA, which controls success or failure of transplants (Yamamura, K., Yoshi, T., Metabolism Highlight, Metabolism 25: 373-380 special ed, Nakayama book, Tokyo).

In serological typing, antiserum of known specificity is added along with complement to lymphocytes to be tested for cytotoxicity. Although serological typing is easy to perform, a subtle difference of an antigen determinant is not identified and thus the presence of subtypes can be often overlooked. Nevertheless, an organ supply of unrelated donors has steadily increased so a new method of testing histocompatibility has been awaited.

HLA antigens are classified into two types, class I and class II. It is suggested that class II antigens DR, DQ and DP are essential for successful kidney transplants. Particularly, DR antigens expressed at the surface of various cells of the body play a key role in histocompatibility (Amamiya, H., Sada, M., Aizawa, H., Composition and function of HLA-D region in Research Report (1984), Statistics of kidney transplants and histocompatibility, the research is supported by Science research fund, 1983 (Comprihensive Research A).

DRw14, a type of known HLA-DR types, is the most difficult type to be defined serologically due to the poor availability of specific antisera. Nucleotide sequence analyses have shown that DRw14 has two subtypes, DRB1*1401 (DRw14-Dw9) and DRB1*1402 (DRw14-Dw16), as classified by cellular HLA typing. (Bodmer, W. F., Albert, E., Bodmer, J. G., Dausset, J., Kissmeyer-Nielsen, F., Mayr, W., Payne, R., Rood, J. J., van, Trnka, Z., and Walford, R. L., 1984, Histocompatibility Testing p4-8, Springer-Verlag, Berlin; Tiercy, J.-M., Gorski, J., Betuel, H., Freidel, A. C., Gebuhrer, L., Jeannet, H., and Mach, B., 1989, J. Hum Immunol 24: 1-14; Gorski, 1989, J. Hum. Immunol 24: 145-149; Kao, H. T., Grgersen P. K., Tang, J. C., Takahashi, T., Wang, C. Y., and Silver, J. 1989, J. Immunol 142:17-43).

Organ transplantation between recipients and donors who are serologically compatible but incompatible with respect to subtypes of DR antigen from each other will cause some problems leading to graft rejection. Thus, serological typing alone may not be clinically useful for organ transplantation.

An object of the present invention is to overcome these disadvantages of serological typing. The invention provides reagents for the HLA-DR typing at the DNA level. More specifically, the invention provides oligonucleotide probes capable of identifying subtypes of a HLA-DR antigen precisely and reagents which include the oligonucleotide probes. Furthermore, the invention provides a method of detecting the HLA-DR subtypes.

SUMMARY OF THE INVENTION

The present invention provides the nucleotide and amino acid sequence of HLA-DRw14c (this allele is referred to as DRB1-14c), an oligonucleotide probe for genetic typing of the DR antigen at the DNA level, a method of genetic typing of the DR antigen using the oligonucleotide probe, an oligonucleotide primer used to amplify a whole or part of the nucleotide sequence of DRB1-14c using a DNA amplification reaction, a DNA probe which recognizes the nucleotide sequence of other types of HLA, at least one different oligonucleotide primer which is used to amplify the nucleotide sequence of other types of HLA, reagents for hybridization and washing, and an instrument and a tool used for the procedure.

DETAILED DESCRIPTION OF THE INVENTION

The present inventors have contemplated that HLA-DR subtypes should be distinguished from among other DR types at the DNA level to overcome the disadvantages of serological typing. Specifically, HLA-DR subtypes can be determined at the DNA level by hybridization of oligonucleotide probes to DNA of HLA-DR subtypes. Oligonucleotide probes are synthesized which are able to hybridize to specific DNA sequences encoding amino acids characteristic to each of the HLA-DR types.

Among the known HLA-DR haplotypes, DRw14 may be one of the most difficult to define serologically because antisera exhibiting unambiguous reactivity with this haplotype are rare.

By a nucleotide sequence analysis of DRw14, we have found that DRw14 has a novel subtype in addition to the known two subtypes, DRw14 (Dw9) and DRw14 (Dw16). We have designated the novel DRw14 subtype as DRB1-14c. Sequence specific oligonucleotide probes are synthesized according to the nucleotide sequences of the DRw14c thus determined, and used for DNA typing of this subtype. We have found that the DRB1-14c is readily identified by the oligonucleotide probes.

The present invention is characterized as follows:

(1) The invention provides an isolated DNA sequence encoding an amino acid sequence as described in SEQ ID No. 1.

(2) The invention provides the isolated DNA sequence of (1) wherein the nucleotide sequence comprises the sequence described in SEQ ID No. 2.

(3) The invention provides a recombinant DNA molecule comprising the 288 or 238 base pair DNA sequence as deduced from SEQ ID No. 1 or as described in SEQ ID No. 2, said DNA sequence being operatively linked to an expression control sequence in said recombinant DNA molecule.

(4) The invention provides the recombinant DNA molecule of (3), wherein said expression control sequence is selected from T7 and T3 promoters.

(5) The invention provides a unicellular host transformed with a recombinant molecule selected from the group consisting of the recombinant DNA molecule of (3).

(6) The invention provides a DNA probe for genetic typing of human leucocyte antigen DR at the DNA level which comprises a single strand of DNA comprising the nuculeotide sequence DRB1-14c as deduced from SEQ ID No. 1 or as described in SEQ ID No. 2.

(7) The invention provide a DNA probe comprising a single strand of DNA for genetic typing of human leucocyte antigen DR at the DNA level which comprises a complementary sequence to the nucleotide sequence DRB1-14c as deduced from SEQ ID No. 1 or as described in SEQ ID No. 2.

(8) The invention provides a single stranded DNA probe for genetic typing of human leucocyte antigen DR at the DNA level which comprises a nucleotide sequence containing at least 10 contiguous bases which is found in the nucleotide sequence of DRB1-14c or the complementary sequence to DRB1-14c as deduced from SEQ ID No. 2 or as described in SEQ ID NO. 1 and which does not hybridize to any nucleotice sequence of chromosomal DNA except for the nucleotide sequence of DRB1-14c and the complementary sequence thereof.

(9) The invention provides the DNA probe of (8) which comprises the nucleotide sequence as described in SEQ ID NO. 3. The nucleotide sequence of SEQ ID No.3 is the sequence of F144.

(10) The invention provides the DNA probe of (8) which comprises the nucleotide sequence as described in SEQ ID No. 4. The nucleotide sequence of SEQ ID No.4 is complementary to the sequence of F142.

(11) The invention provides the DNA probe of any one of (6)–(10) which is labelled with radioisotope, a fluorescent substance, color former, luminescent substance, or any combination thereof.

(12) The invention provides the DNA probe of any one of (6)–(10) comprising the oligonucleotide immoblized on a membrace.

(13) The invention provides a method for amplifying all or part of the nucleotide sequence of DRB1-14c as deduced from SEQ ID No. 1 or as described in SEQ ID NO. 2 which comprises the steps of
(a) annealing an oligonucleotide primer with heat denatured genomic DNA isolated from the peripheral blood of a DRB1-14c individual in the presence of TAQ polymerase,
(b) heating the annealed DNA to allow for primer extension and
(c) repeating steps (a) and (b), (14) The invention provides the method of (13) wherein the oligonucleotide primer is labelled with radioisotope and/or a substance selected from the group consisting of a fluorescent substance, color former and luminescent substance.

(15) The invention provides the method of (13) wherein the oligonucleotide primer of step (a) is capable of hybridizing to radioisotope- or color former-labelled nucleic acid during the DNA amplification.

(16) The invention provides the method of (13) wherein the oligonucleotide primer is selected from the group consisting of oligonucleotide primers having the nucleotide sequence as described in SEQ ID No. 5, SEQ ID No. 6 and SEQ ID No. 7.

(17) The invention provides the method of (13) wherein the oligonucleotide primer is selected from oligonucleotide primers having the nucleotide sequence as described in SEQ ID No. 3 and SEQ ID No. 4.

(18) The invention provides a reagent for genetic typing of human leucocyte antigen comprising at least 10 contiguous nucleotide bases which are found in the nucleotide sequence of DRB1-14c or the nucleotide sequence complementary to that of DRB1-14c and a DNA probe which hybridizes to the nucleotide sequence of other types of human leucocyte antigens.

(19) The invention provides a genetic typing kit for human leucocyte antigen comprising the reagent of (18) and reagents for hybridization and washing.

(20) The invention provides the genetic typing kit for human leucocyte antigen according to (19) further comprising an instrument and a tool used for the hybridization procedure.

(21) The invention provides a genetic typing kit for human leucocyte antigen comprising the reagent of (18) and an oligonucleotide primer capable of amplifying a whole or part of the nucleotide sequence of DRB1-14c as deduced from SEQ No. 1 or as described in SEQ ID No. 2.

(22) The invention provides the genetic typing kit for human leucocyte antigen according to (21) further comprising reagents for hybridization and washing.

(23) The invention provides the genetic typing kit for human leucocyte antigen according to (22) further comprising an instrument and a tool used for the hybridization procedure.

(24) The invention provides a reagent kit for human leucocyte antigen comprising at least one DNA probe comprising all or part of the nucleotide sequence DRB1-14c as deduced from SEQ ID No. 1 or as described in SEQ ID No. 2, an oligonucleotide primer capable of amplifying a whole or part of the nucleotide sequence of DRB1-14c as deduced form SEQ ID No. 1 or as described in SEQ ID No. 2, a DNA probe which hybridizes to the nucleotide sequence of other types of human leucocyte antigen and at least one oligonucleotide primer which is capable of amplifying the whole or part of the nucleotide sequence of said other types of human leucocyte antigen.

(25) The invention provide the reagent kit for human leucocyte antigen of (24) further comprising reagents for hybridization and washing.

(26) The invention provide a method of genetic typing which comprises the step of hybridizing denatured and immobilized test DNA with a DNA probe comprising at least 10 contiguous bases of the nucleotide sequence of DRB1-14c of the complementary sequence of DRB1-14c as deduced from SEQ ID No. 1 or as described in SEQ ID No. 2.

The present invention includes DNA probes, which are substantially homologous to at least a portion of a hypervariable DNA region located in the second exon of the DRB1-14 allele. Especially suitable probes include F144 and F142. When used to probe Southern blots of restriction enzyme digested genomic DNA, or amplified DNA fragment which includes a whole or part of the second exon of a DRB gene these probes only hybridize to DNA from DRB1-14c individuals but fail to hybridize to DNA from DRB1*1401 or DRB1*1402 individuals. Thus, these probes are useful in HLA typing. In a preferred embodiment, the oligonucleotide probe contains at least 10 contiguous bases as found in DRB1-14c. In the present invention, the reagent kit includes probes or oligonucleotide probe immobilized on membranes and reagents for PCR, hybridization, washing of membrane, and detection. The genetic typing kit includes reagent kits, tools and equipments.

The present invention will be further described by the nucleotide sequence of the novel DRB1-14c, its use, and a genetic typing method.

Figures 1, 1A:
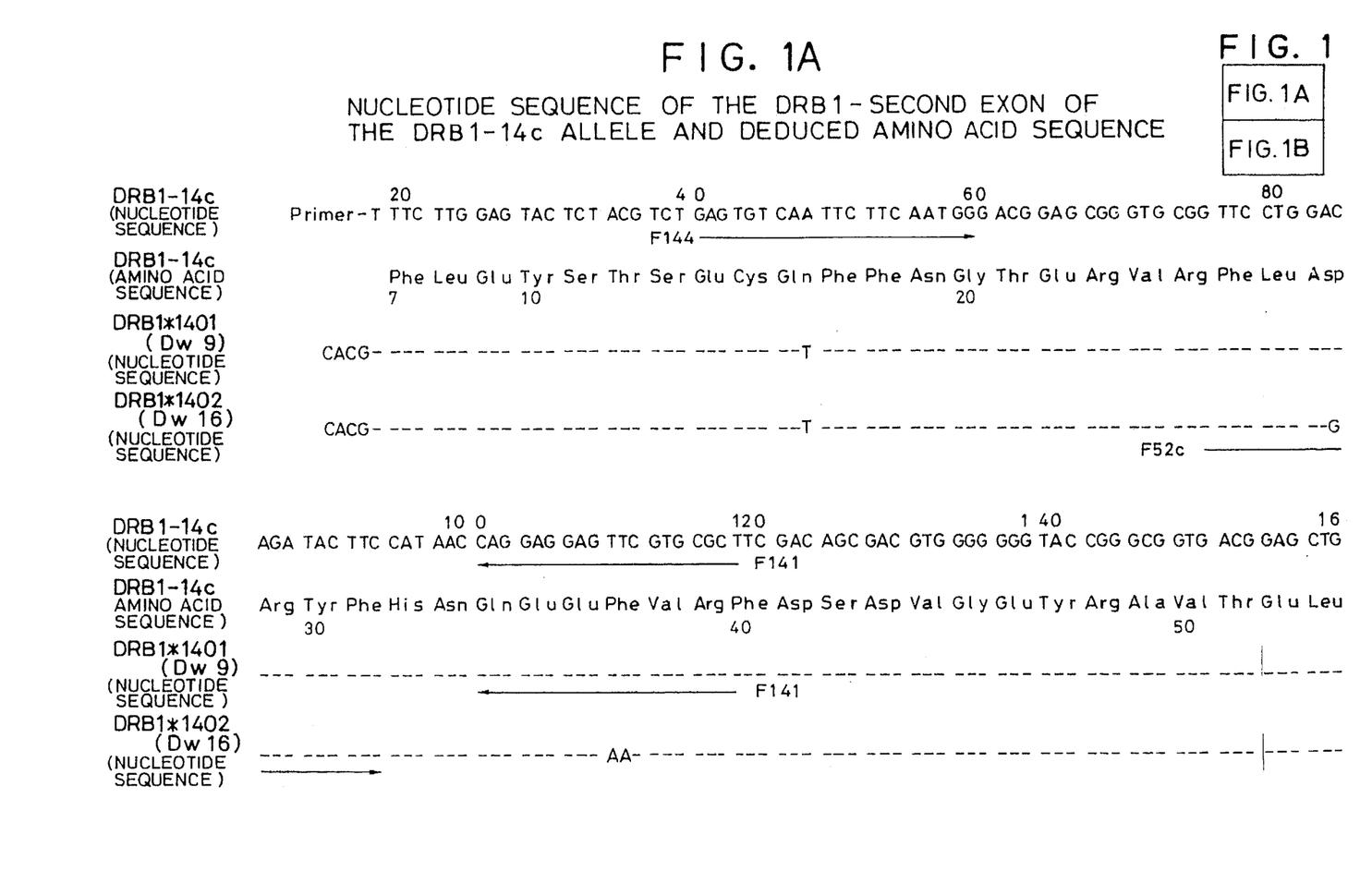
FIG. 1A shows a nucleotide sequence of the second exon of the DRB1-14c gene from nucleotide 19 to nucleotide 16 (SEQ ID No.2), and the corresponding amino acid sequence (SEQ ID No. 1).
Figure 1B:
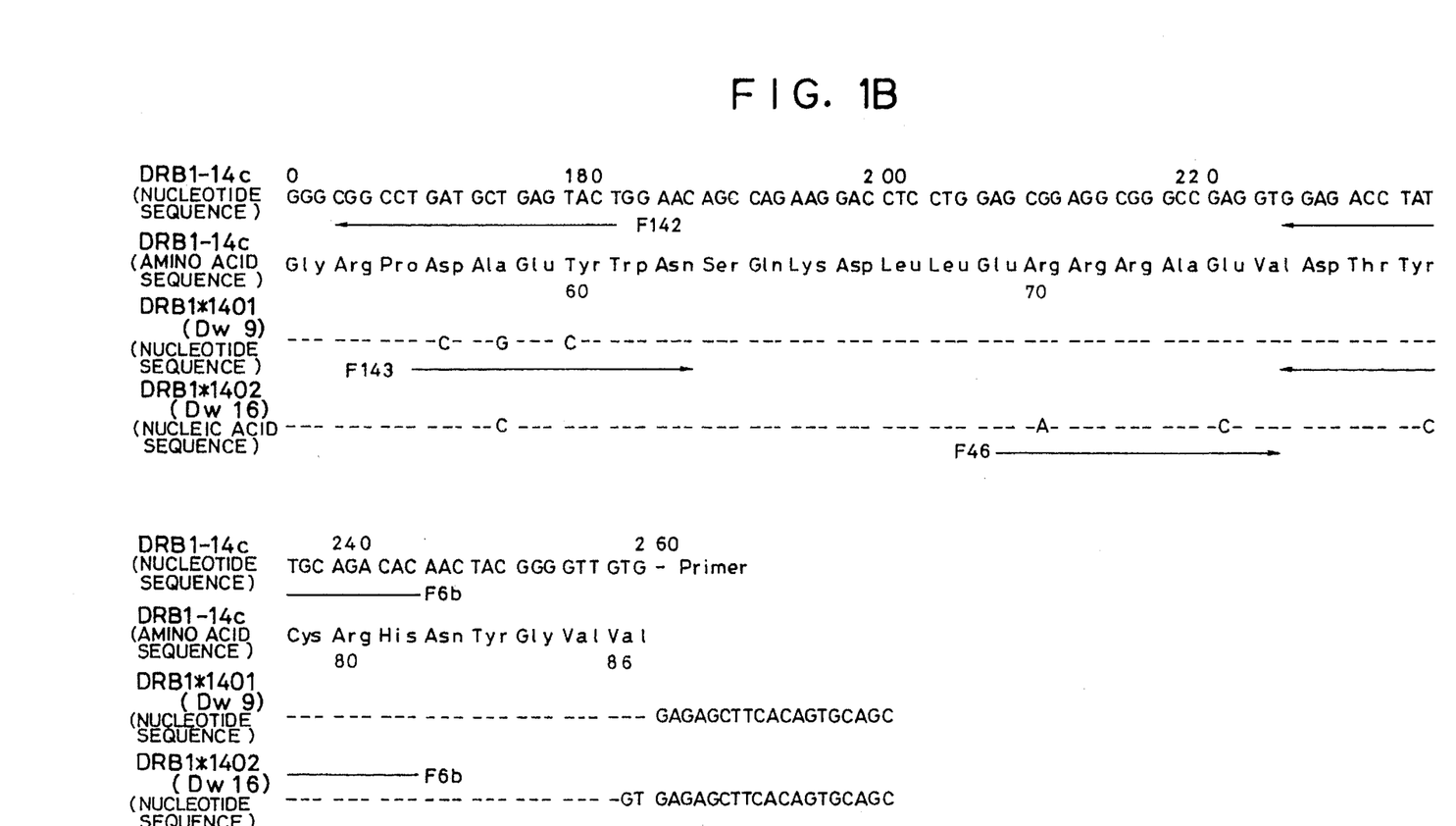
FIG. 1B shows the nucleotide sequence of the second exon of DRB1-14c from nucleotide 162 to nucleotide 260 (SEQ ID No.2), and the corresponding amino acid sequence.

The nucleotide sequence of DRB1-14c is described in connection with an amino acid and nucleotide sequence as shown in FIG. 1. In FIG. 1, an oligonucleotide probe hybridizes to an underlined sequence; the right-pointed arrow indicates the 5'-3' direction of the nucleotide sequence of DRB1-14c; and the left-pointed arrow indicates the complementary sequence thereof.

The nucleotide sequence of DRB1-14c is determined as follows:

HLA-DR sera are harvested from Japanese volunteers and tested for subtypes using a serum listed in The Tenth International Histocompatibility Antigen Workshop. A subtype which reacts with at least two sera of three anti-DRw 14 sera (serum 9060, 9061, 1111) and with anti-DR1/2/w6 serum, but does not react with anti-DRw13 sera (serum 9058, 9062) is designated as DRw14.

The chromosomal DNA of DRw14 is subjected to polymerase chain reaction (PCR) using oligonucleotide primers such as GH46, FPR1, and DRβAMP1. The resulting DNA is then hybridized to oligonucleotide probes such as F143, F6, F46, F141, and F52. The nucleotide sequences of these primers and probes are described in SEQ ID No 5, 6, 7, 8, 9, 10, 11, 12, respectively. Almost all of the sequence of the second exon (288 bp) of a DRB gene is amplified with oligonucleotide primers, GH 46 and DRβAMP1, and the second and the third hypervariable regions (238 bp) of the second exon of the DRB gene is amplified with oligonucleotide primers, FRP1 and DRβAMP1(Obata, F., Abe, A., Ohkubo, M., Ito, I., Kaneko, T., Otani, F., Watanabe, K., and Kashiwagi, N. 1990: Hum Immunol 27: 269–284).

After DNA amplification, the DNA fragment is subjected to an alkaline denaturation and blotted onto a nylon membrane. A $^{32}$P-labelled oligonucleotide probe is hybridized to the DNA blotted on the membrane. After hybridization, nylon membranes are washed in a solution (6× SSC, 0.9M NaCl, 0.09M sodium citrate, 0.1% SDS) at room temperature for 5 minutes. Each membrane is then washed again as follows: membrane hybridized to oligonucleotide F 143 is washed fit 54° C. for 15 minutes; F 144 (see DRw14 detection infra) or F 52c at 58° C. for 15 minutes; F52c at 58° C. for 15 minutes; F6b, F141, F142 (see DRw 14 detection infra) or F46 at 62° C. for 15 minutes. Oligonucleotide probes are synthesized for genetic typing of HLA-DRw14 according to the nucleotide sequence of known sequences such as DRB1*1401(DRw14-Dw 9) and DRB1*1042 (DRw14-Dw16) (Tiercy, J.-M., Gorski, J., Betuel, H., Freidel, A. C., Gebuhrer, L., Jeannet, H., and Mach, B. : 1989, 24; 1–14., Hum Immunol., Gorski, J. : 1989, 24; p.145–149., Kao, H. T., Gregersen, P. K., Tang, J. C., Takahashi, T., Wang, C. Y., and Silver, J.: 1989, 142; p.1743, J Immunol).

The nucleotide sequences of the oligonucleotide probes, F6b, F141, F143 are complementary to that of DRB1 (DRB1*1401) and the sequences of the oligonucleotide probes, F46, F52c are complementary to that of DRB1 (DRB1*1402). The nucleotide sequences of some of these oligonucleotide probes are complementary to those of some DRB1and DRB3 as well as DRB1*1401 and DRB1*1402 (Table 1)

TABLE 1

| Oligonucleotide probes | Specificity of oligonucleotide probes | | |
|---|---|---|---|
| | DRB1 allele | | |
| | DRw14 associated | other DR associated | DRB3 allele |
| Fb6 | DRB1* 1401, DRB1-14c | DRB1* 1201, DRB1-12b | |
| F141 | DRB1* 1401, DRB1-14c | DRB1* 0701 | DRB3* 0301 |
| F142 | DRB1-14c | | |
| F143 | DRB1* 1401 | | |
| F144 | DRB1-14c | | |
| F46 | DRB1* 1402 | DRB1* 0101, DRB1* 0102, DRB1* 0404 FRB1* 0405, DRB1* 0408 | |
| F52c | DRB1* 1402 | DRB1-JX6 | |

Specificity of these oligonucleotide probes is determined by genetic typing of B-cell lines whose DR/D phenotypes and DRB1/B3/B4 genotypes have been well characterized and of Japanese volunteers typed serologically as DRw14. (Table 2).

Established B cell lines are reported in The Ninth and Tenth International Histocompatibility Antigen Workshop (Schreuder, G. M. T., Doxiadis, L. Parievliet, J., and Grosse-Wilde, 1984: p.243–174H. Histocpmpatibility Testng, Spriger-Verlag Berlin., Jaraquemada, D., Reinsmoen, N. L., Ollier, W., Oloye, R., Bach, F. H., and Festenstein, H.: 1984, p.270–174., Histocompatibility Testing, Springer-Verlag Berlin., Yang, S. Y., Milford, E., Hmmerling, U., and Dupont, B.: 1989, 1; p.11–19, Immunobiology of HLA, Spring-Verlan, New York).

The hybridization results are shown in Table 2.

TABLE 2

Genetic typing of B cell lines and heterozygous Japanese volunteers

| | | Phenotype | | Genotype | | Oligonucleotide probe | | | | |
|---|---|---|---|---|---|---|---|---|---|---|
| | | DR | D | DRB1 | DRB3/4 | F6b | F141 | F143 | F46 | F52c |
| | | | | Homozygous B cells | | | | | | |
| TEM | (C) | w14 | w9 | DRB1*1401 | DRB3*0201 | + | + | + | | |
| 31227ABO | (C) | w14 | w9 | (DRB1*1401 | DRB3*0201) | + | + | + | | |
| AMALA | (AI) | w14 | w16 | DRB1*1402 | DRB3*0101 | | | | + | + |
| LZL | (AI) | w14 | w16 | DRB1*1402 | DRB3*0101 | | | | + | + |
| BIN40 | (C) | 4 | w14 | DRB1*0404 | DRB4*0101 | | | | + | |
| KT3 | (J) | 4 | w15 | DRB1*0405 | DRB4*0101 | | | | + | |
| JESTHOM | (C) | 1 | w1 | (DRB1*0101) | | | | | + | |
| KT11 | (J) | w13 | w19 | (DRB1*1302 | DRB3*0301) | | + | | | |
| MOU | (C) | 7 | w17 | (DRB1*0701 | DRB4*0101) | | + | | | |
| BM16 | (C) | w12 | DB6 | (DRB1*1201 | DRB3*0201) | + | | | | |
| | | | | Heterozygous Japanese | | | | | | |
| KW | (J) | w14, 9 | | | | | | | | |
| 24F | (J) | w14, w8 | | | | + | + | + | | |
| 38F | (J) | w14, w11 | | | | + | + | + | | |
| 59M | (J) | w14, 9 | | | | + | + | + | + | + |
| 75M | (J) | w14, w8 | | | | | | | + | + |
| 38M | (J) | w14, 4 | | | | + | + | + | | |
| 36M | (J) | w14, w15(2) | | | | + | + | | | |
| 26F | (J) | w14, 9 | | | | + | + | | | |

C: Caucasian
AI: Native Americans
J: Japanese

As shown in Table 2, DNA from Japanese volunteers KW(DRw14/9), 24F (DRw14/w8), and 38F (DRw14/w8), and 38F (DRw14/w11) is hybridized to F6b, F141, and F143. This profile of hybridization is identical to that of B cell lines (TEM and 31227ABO) having the DRB 1*1401 allele, and therefore, three Japanese volunteers are likely to have the DRB*1401 genotype. On the other hand, DNA from Japanese volunteers 59M (DRw14/9) and 75M (DRw/w8) is hybridized to F46 and F52c. This profile of hybridization is identical to that of B cell lines (AMALA and LZL) having the DRB*1402 allele, suggesting that the Japanese volunteers have the DRB*1402 genotype.

In contrast to the above Japanese volunteers whose DR genotypes are explained by the known DRw14-related alleles, Japanese volunteers 38M (DRw14/w15), and 26F (DRw14/9) give a novel profile of hybridization in genetic typing (Table 2). DNA from these Japanese volunteers is not hybridized to F143, one of the characteristic to the DRB 1*1401 allele, although the DNA is hybridized to F6b and F141 as is the DNA of the DRB1401 allele. These results indicate that the three Japanese volunteers have a DRw14 genotype different from that of the DRB1*1401 allele at least in the target sequence of F143. The genotype of the DRw14 related allele of these Japanese volunteers is different either from that of the DRB1*1402 allele, because the DNA from Japanese volunteers 36M and 26F is not hybridized to F46 and F52c, and the DNA from Japanese volunteers 38M is not hybridize to F52c (Table 2). Taken altogether, the genetic typing indicates that there exist the third DRw14-related allele in the Japanese, population in addition to the two known DRw14-related alleles, DRB1*1401 and DRB1*1402. The third DRw14-related allele is referred to DRB1-14c for convenience.

Sequence Analysis of the DRB1-14c Allele.

To determine the primary sequence of the DRβ1 chain of the DRB1-14c allele, chromosomal DNA isolated from the Japanese volunteers 36M and 38M typed as DRB1-14c in genetic typing is subjected to PCR with primers GH46 and DRβAMP1. The amplified DNA fragment containing the second exon of the DRB genes is ligated into a plasmid vector and cloned in bacteria. According to the results of genetic typing described above, F6b is used to identify bacterial clones containing the DRB1-second exon of the DRB1-14c allele. Three clones from each of the Japanese volunteers 36M and 38M have a nucleotide sequence identical to each other. In keeping With the results of genetic typing, the nucleotide sequence of the DRB1-14c allele contains sequences of F6b and F141 but not those of F143, F46, or F52c (FIG. 1). In addition, the DRB1-14c allele has a unique base change (adenine at base No. 48) that is not detectable in the genetic typing described above.

It is unlikely that the sequence determined here originates from the DRB3 gene associated with the DRB1-14c allele, because the analysis of one F6b-negative clone from the donor 38M (DRB1-14c/4) reveals that the Japanese volunteer's DRB3 gene associated with the DRB1—14c allele has a sequence (not shown) identical to that of the DRB3*0201 (DRw52b) allele (Gorski, J. and Mack, B.,1986, Nature 322: 67–70) and distinct from the sequence presented here. It is unlikely either that the sequence determined here originates from a pseudogene, DRB2, because the DRB2 gene of DR haplotypes belonging to a "DRw52 family" such as DRw11, DRw12, DRw13, DRw14, DRw17 and DRw18 are reported to lack the second exon (Rollini, P., Mach, B., and Gorski, J., 1987, Immunogenetics 25: 336–342) and it may be reasonable to asume that the same is true for the DRB2 gene associated with the DRB1-14c allele. Therefore, the nucleotide sequence presented here is considered to originate from the DRB1 gene but not from the DRB2 or DRB3 genes associated with DRB1-14c allele.

The amino acid sequence in the first domain of the DRB1 chain of the DRB1-14c allele deduced from the nucleotide sequence differs from the first domain sequence of the DRB1*1401allele (Tiercy, J.-M., Gorski, J., Betuel, H., Freidel, A. C., Gebuhrer, L., Jean net, M., and Mach, B., 1989, Hum Immunol 24 145–149; Gorski, J., 1989. Hum Immunol 24: 145–149) at three positions at amino acids No. 16, 57, and 60 (FIG. 1) The glutamine at position 16 is unique to the DRB1-14c allele and is not found in other DR haplotypes sequenced so far. The positions 57 and 60 are the target sequence of F143 that distinguishes the DRB1-14c allele from the DRB1*1401 allele in genetic typing. The amino acid sequence of the DRB1-14c allele differs from that of the DRB1*1402 allele (Kao, H. T., Gregersen, P. K., Tang, J. C. Takahashi, T., Wng, C. Y., and Silver, J., 1989, J Immunol 142 1743; Gorski, J., 1989, Hum Immunol 24: 145–149) at six positions amino acids No. 16, 28, 37, 70, 74, and 86. The position 28 is the target sequence of F52c and the positions 70 and 74 are the target sequence of SSO F46. By comparing among the DRB1 sequences of the three DRw14-related alleles as well as comparing them to the DRB1 sequence of other DRB1 alleles such as DRB1*1301 (DRw13-Dw18) (Tiercy, J.-M., Gorski, J., Betuel, H., Freidel, A. C., Gebuhrer, L., Jean net, M., and Mach, B., 1989, Hum Immunol 24: 1–14; kao, H. T., Gregersen, P. K., Tang, J. C., Takahashi, T., Wang, C. Y., and Silver, J., 1989, J. Immunol 142: 1743), DRB1*1302 (DRw 13-Dw19) (Tiercy, J.-M., Gorski, J., Betuel, H., Freidel, A. C., Gebuhrer, L., Jean net, M., and Mach, B., 1989, Hum Immunol 24: 1–14), and DRB1-X6 (Obata, F., Abe, A., Ohkubo, M., Ito, I., Kaneko, T., Otani, F., Watanabe, K., and Kashiwagi, N., 1990 Hum Immunol 27: 269–284) we are unable to identify the amino acid residue that explain the serologic DRW14 specificity. In other words, there is no polymorphic amino acid residue that is common only to the three DRw14-related alleles.

Genetic Typing of the DRB1-14c Allele.

In the genetic typing described above, the DRB1-14c allele is distinguish from the DRB1*1401by a negative hybridization to F143. To identify the DRB1-14c allele positively in genetic typing, we next synthesized oligonucleotide probes directed toward the unique sequence of the DRB1-14c allele. F144 is directed to the glutamic acid at position 16 that is unique to the DRB1-14c allele. (Table 1 and FIG. 1). F 142 is directed to the aspartic acid at position 57 and tyrosine at position 69 that are common to many other DRB1 alleles including the DRB1*1402, DRB1*1301, DRB1*1302, and DRB1-JX6, but F142 is nevertheless specific to the DRB1-14c allele because of the silent mutation (thymine at base No. 174) that is unique to this allele.

Figure 2:
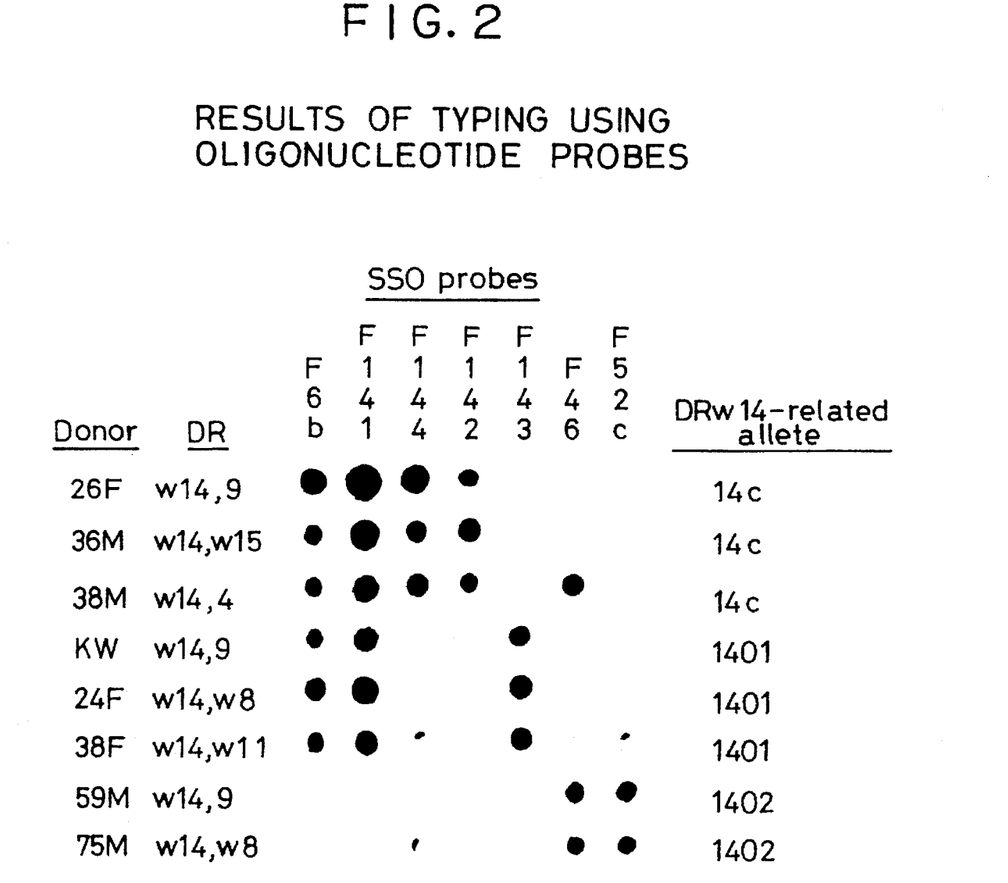
FIG. 2 shows a genetically typed DR antigen using oligonucleotide probes of the invention.

Chromosomal DNA is isolated from Japanese volunteers who have the serologic DRw14 as well as other DR specificities and is subjected to PCR using GH46 and DRβAMP1 to amplify the DRB second exon including the first hypervariable region. The amplified DNA fragments are dot-blotted to a nylon membrane arid hybridized to each of F142, F144 as well as F6b, F141, F143, F46 and F52c. As shown in FIG. 2 and Table 3, we have found that DNA from several Japanese donors who have the serologic DRw14 specificity hybridized to the DRB1-14c-specific F142 and F144 as well as F6b and F141, indicating that these Japanese volunteers have the genotype of the DRB1-14c allele. The DRw14-related allele of other Japanese volunteers are typed as either DRB1*1401 or DRB1*1402 according to their profile of hybridization with SSO probes, in which SSOs specificities directed to the DRB1 and DRB3 alleles other than DRw14-related alleles (Table 1) are also taken into consideration.

TABLE 3

Genetic typing of DRw14 related alleles in Japanese volunteers using the oligonucleotide probes

| Test subjects | DR phenotype | oligonucleotide probe | | | | | | | DRw14 associated allele |
|---|---|---|---|---|---|---|---|---|---|
| | | F6b | F141 | F144 | F142 | F143 | F46 | F52c | |
| 36M | w14, w15(2) | + | + | + | + | | | | 14c |
| 82F | w14, w15(2) | + | + | + | + | | | | 14c |
| 26F | w14, 9 | + | + | + | + | | | | 14c |
| MS | w14, 9 | + | + | + | + | | | | 14c |
| GOT | w14, w11 | + | + | + | + | | | | 14c |
| #128 | w14, w12 | + | + | + | + | | | | 14c |
| 13M | w14, w13 | + | + | + | + | | | + | 14c |
| SUZU | w14, 1 | + | + | + | + | | + | | 14c |
| 38M | w14, 4 | + | + | + | + | | + | | 14c |
| 55F | w14, 4 | + | + | + | + | | + | | 14c |
| AL1 | w14 | + | + | + | + | + | | | 14c/1401 |
| SER | w14 | | + | + | + | + | | | 14c/1401 |
| 7M | w14, w11 | + | + | | | + | | | 1401 |
| IIT | w14, w12 | + | + | | | + | | | 1401 |
| KW | w14, 9 | + | + | | | + | | | 1401 |
| 24F | w14, w8 | + | + | | | + | | | 1401 |
| 38F | w14, w11 | + | + | | | + | | | 1401 |
| 40M | w14, w8 | + | + | | | + | | | 1401 |
| SEKI | w14, 1 | + | + | | | + | + | | 1401 |
| 32M | w14, 4 | + | + | | | + | + | | 1401 |
| 59M | w14, 9 | | | | | | + | + | 1402 |
| 75M | w14, w8 | | | | | | + | + | 1402 |
| 57F | w14, w8 | | | | | | + | + | 1402 |
| 80F | w14, 4 | | | | | | + | + | 1402 |
| ST | w15(2), -(JX6) | | | | | | | + | |
| IMA | w15(2), w13 | | | | | | | + | |
| FO | w8, w12 | + | | | | | | | |
| TK | 7, 4 | | | | + | | | | |
| KU | w8, 9 | | | | | | | | |
| 8CF | w15(2), w17(3) | | | | | | | | |

Test Samples of the Invention

The oligonucleotide probes of the invention are part of the nucleotide sequence encoding polypeptide expressed on the surface of cells and may be used for detection of mRNA and cDNA as well as chromosomal DNA. mRNA, cDNA, and chromosomal DNA are prepared according to conventional methods and a suitable method of preparing these nucleic acids is chosen according to the source of samples and procedures following the DNA preparation. When necessary, nucleic acid to be tested can be amplified by PCR to detect nucleic acid of interest more easily. The oligonucleotide probes described above or oligonucleotides having a sequence different from the probes may be used as primers. The latter oligonucleotides are typically used as primers. After amplification, the nucleic acids are digested with more than one restriction enzyme and the restriction fragments are gel-electrophoresed. The DNA fragments thus obtained are tested for the presence of DNA of interest using the oligonucleotides of the invention(RFLP approach).

Form of Oligonucleotides Used for Hybridization

The oligonucleotide probes may be used as a chemically bonded form, a physically immobilized form, or a solubilized form in solution or suspension. Any form of the oligonucleotides may be utilized. Specifically, the oligonucleotide probes of the invention are used as follows: (1) An amount of the oligonucleotide probes in excess of the DNA of interest is dissolved in solution or suspension and used for hybridization. A gene of interest or a DNA fragment of interest is first immobilized on a membrane and then the oligonucleotide is hybridized to the immobilized sample. After hybridization, an unhybridized oligonucleotide probe is removed and tested. (2) In addition to the oligonucleotide of the invention, at least more than one type of an oligonucleotide probe is prepared which hybridizes to a different region(s) of the DNA of interest, which is immobilized on a membrane for hybridization. (3) A nucleotide sequence is prepared which is linked to the oligonucleotide of the invention at its 5' or 3' end and the complementary sequence to this sequence is immobilized on a membrane for hybridization.

Any material can be used to immobilize nucleic acid of interest or oligonucleotide probes. A form of the material may be a membrane, plate, or strip, for example. A membrane is preferable. Membranes used in the invention are commercially available materials, such as nylon membranes or membranes made from cellulose. For example, Hybond™-C, Hybond™-C Super, Hybond™-ECL, Hybond™-N, Hybond™-N+(Amersham), Whatman 541 filter (Whatman paper, Ltd.); Duralon™UV (STRATAGENE), Photo Gene™Nylon Membranes (BRL), Duralose-UV™ (STRATAGENE) and any other material capable of immobilizing a gene, gene fragments or oligonucleotides may be used as a membrane. The membrane is heated, exposed to UV-light or treated with any suitable means for immobilizing nucleic acid or oligonucleotides. The method of treating the membrane is dependent upon the properties of the particular membrane (e.g., Hybond-N+ is exposed to UV-light for immobilization; Hybond-C extra is 80° C. under vacuum).

It is preferable to modify the 5' or 3' end of a fragment of a gene or oligonucleotide probes using poly-dT or a linker: the 3' end is modified using terminal deoxynucleotide transferase or oligonucleotides and ligase. The 5' end is modified using a 5' primer used for amplification of the nucleic acid of interest, In order to detect the hybridization, oligonucleotide probes or fragments of gene of interest are labelled with radioisotope, or a fluorescent substance or are modified to be labelled with other substances. Hybridization is tested by the presence of labelling substances. Labelling substances comprise radioisotope, such as $^{32}P$, $^{35}S$ and $^{125}I$ and non-radioisotope substance, such as fluorescein isothiocyanate, biotin, and digoxigenin.

In the detection step, radioactivity on some materials such as membranes on which hybridization is performed is measured by exposing it to X-ray film, and fluorescence is measured by photometer, and in the case of biotin or digoxigenin, such as color or luminescence produced by enzyme-linked immunoassay using streptavidin conjugate or anti-digoxigenin conjugate is measured by photometer or by exposing to X-ray film, respectively. In the enzyme-linked immuno-assay, enzymes such as alkaline phosphatase and horseradish peroxidase can be used.

Labelling can be carried out during an oligonucleotide synthesis or amplification of a gene of interest using an appropriately prepared nucleic acid. Alternatively, labelling can be done at the 5' or 3' end or within oligonucleotide probes or a gene of interest which is premodified for labelling. These labelled oligonucleotides or genes of interest may be used for genetic typing of HLA-DR.

Kit for Genetic Typing of HLA-DR

A kit for genetic typing of HLA-DR includes reagents such as oligonucleotide probes or oligonucleotide probe immobilized membranes, a reagent for labelling, membranes for immobilizing oligonucleotide probes or a gene of interest, or a reagent for hybridization, a washing reagent for membranes, a reagent containing a positive or negative control to determine hybridization, an evaluation standard for results and interpretation of data, and relevant instruments and tools for hybridization detection or washing procedures. A reagent for labelling comprises PhotoGene™Nucleic Acid Detection System (BRL, Life Technologies, Inc.,) which contains streptavidin-alkalin phosphatase, nylon membrane, 4-methoxy-4-(3-phosphate phenyl-1)spiro(1,2-dioxethane-3,2'-adamantane) and 2-amino-2-methyl-1-propanol, or DIG system™ (Boehringer Mannheim) contains digoxigenin anti-digoxigenin fluorence, anti-digoxigenin alkaline phosphatase and anti-digoxigenin peroxidase. Tools and instruments comprise plastic tubes (such as BIO-BIK Sampling tube, Bio Plastic Co., Ltd.), borosilicated glass tube (Corning Glass Works), adjustable volume digital pipets (such as Pipetman™, Gilson) and tips for them, heat-sealable plastic bags (supplied by Cosmo Bio and so on), a photometer to detect the developed luminescence, fluorescence, or color, x-ray films, exposure cassettes, and film hangers (supplied by Fuji medical Systems Co., Ltd. and so on), and constant temperature oven or water bath. The kit contains a whole or part of the materials, but it contains at least oligonucleotide probes or oligonucleotide immobilized membranes. Reagents are provided as concentrates and a concentration of reagents can be adjusted, although reagents can be stored in a concentration suitable for immediate use.

Different types of oligonucleotide probes are required for genetic typing of HLA-DR. It is desirable for an accurate measurement and ease of manipulation that a reagent should also contain known oligonucleotide probes to detect known types of HLA-DR, in addition to DRB1-14c.

The present invention provides the following benefits.

DRw14 associated genes can be genetically typed at the DNA level using DRB1-14c sequence specific oligonucleotide probes such as F142 and F144 as well as other oligonucleotide probes. According to a survey of 361 Japanese Volunteers, a genetic frequency of DRB1-14c, DRB1*1401, and DRB1*1402 is 0.018, 0.038, and 0.017, respectively, suggesting that a frequency of DRB-14c is one fourth of the frequency of DRw14 associated genes and that genetic typing of the invention is extremely useful for complete genetic typing of DR antigens. We have found a novel subtype DRw14c and determined the nucleotide sequence thereof. The discovery of DRB1-14c may be therapeutically useful and may contribute to diagnosis of HLA antigens.

EXAMPLES

The invention will be further described by the Examples, which are not intended to limit the scope of the invention.
DNA Sequencing of Second Exon of DRB1-14c Chromosomal DNA of a serologically DRw14 type, KW (DRw14/9), 24F (DRw14/w8) and 38F (DRw14/w11) was prepared from peripheral blood of three Japanease volunteers according to the method described by Maniatis, T., Fritsch, E. F., Sambrock, J., et.al., in Molecular Cloning: A Laboratory Manual, 1987, p280–281, Cold Spring Harbor Lab., Cold Spring Harbor, N.Y.

Chromosomal DNA was amplified by PCR as follows: 48 ul of a solution containing 1ug of chromosomal DNA, primers (0.5 uM each), dNTP (20 um of each of dATP, dCTP, dGTP, dTTP), 10 mM Tris-HCl/pH 8.0, 3mM $MgCl_2$, 0.05% Tween 20 and 0.05% NP-40 was heated at 98° C. for 5 minutes to denature the chromosomal DNA. After denaturation, 2 ul (2.5 unit/ul) of Taq I DNA polymerase was added to the solution. 40 ul of mineral oil was layered onto the mixture. The mixture was heated at 55° C. for 2 minutes to anneal the primer to chromosomal DNA. The mixture was heated at 72° C. for 2 minutes for primer extention, followed by a 29-cycle amplification (DNA denaturation at 95° C. for 1 minute, annealing at 55° C. for 1 minute, primer extention at 72° C. for 3 minutes). After amplification, the DNA fragment was alkaline-denatured and blotted onto a nylon membrane. A $^{32}$P-labelled oligonucleotide probe was hybridized to the DNA blotted on the membrane according to the method as described by Obata, F., Ito, I., Kaneko, T., Ohkubo, M., Ishimoto, A. L., Abe, A., and Kashiwagi, N.: 1989, 33; p.550–558, Tissue Antigens. The oligonucleotide probes were synthesized according to the nucleotide sequence of DRB1*1401 (DRw14-Dw9), DRB1*1042 (DRw14-Dw16) and the resulting oligonucleotide was purified by electrophoresis. The nucleotide sequences of probes, F6b, F141, F143 were complementary to the sequence of DRB1*1401. The nucleotide sequence of probes, F46 and F52c were complementary to the sequence of DRB1*1402.

After hybridization, the nylon membrane was washed in a washing solution (6× SSC, 0.9M NaCl, 0.09M sodium citrate, 0.1% SDS) at room temperature for 5 minutes. Each membrane was then washed again in fresh washing solution: the membrane probed with F143 probe was washed at 54° C. for 15 minutes; F144, F52c at 58° C. for 15 minutes; F6b, F141, F142, F46 at 62° C. for 15 minutes. The results are shown in Table 2. The DRβ1 chain gene of DRB1-14c was cloned as follows: The 288 bp DNA fragment amplified by PCR was digested with BamHI (GH 46 contains the restriction site). The restriction fragments were electrophoresed through a 1.5% agarose gel and the DNA fragments were purified according to a known method. The DNA fragments were inserted into the BamHI-EcoRV site of the Bluescript plasmid (Stratagene). E. coli JM109 [recA1, supE44end A1hsd R17 gyrA96 relA1thi Δ(lac-proAB)F'[traD36 prAB+ lacI$^q$lacZ ΔM15] was transformed with the recombinant plasmid and then grown on solid LB agar plate (1% bactotryptone, 0.5% yeast extract, 1% NaCl, and 1.5% bactoagar) containing 5-bromo-4-chloro-3-indole-β-D-galactopyronoside (X-gal) and isopropyl-β-D-(–)-thiogalactoside (IPTG). After incubation, white colonies were picked with toothpicks and transferred to a nitrocellulose filter. The DNA was fixed on the membrane according to the method described by Grunstein, M., Wallis, I., et.al., (Meth. Enzymology: 1979, 63; p.379–389, Academic Press, New York). The probe was hybridized to the DNA on the membrane according to the method described by Obata, F., Ito, I., Kaneko, T., Ohkubo, M., Ishimoto, A. L., Abe, A., Kashiwagi, N.: 1989, 33; p550–558, Tissue Antigens). For identification of the DNA of the DRβ gene of DRw14 haplotype, a $^{32}$P-labelled F6b probe was used for colony hybridization. The F6b probe has been reported by Abe, et.al., (Abe, A., Ito, I., Ohkubo, M., Kaneko, T., Ito, K., Kato, H., Kashiwagi, N., and Obata, F.: 1989, 30; p.422–426, F. Immunogenetics), and basically has the same sequence as that of DRB1-14/b as described by Tiercy, J.-M., Gorski, J., Betuel, H., Freidel, A. C., Gebuhrer, L., Jeannet, H., and Mach, 1989: 24; p.1–14, B. Hum Immunol. The DNA of a transformant which hybridized to F6b was sequenced according to a dideoxy method as described by Sanger, F., Nicklen, S., Coulson, A. R., et.al., in Proc. Natl. Acad. Sci. U.S.A., 1977, 74; p.5463–5467.

An E. coli JM109 transformant having the nucleotide sequence of DRB1-14c was designated as pDR14c (38M-103F). pDR14c was deposited with Fermentation Research Institute, Agency of Industrial Science and Technology and was assigned the accession number FERM 11668.

FIG. 1 shows the nucleotide sequence of the second exon of a DRB1 gene and deduced amino acid sequence. Two DRw14 genotypes, DRB1*1401 and DRB1*1402 are known. (Bodmer, W. F., Albrt, E., Bodmer, J. G., Dausset, J. J., Kissmeyer-Nielsen, F., Mayr, W., Payne, R., Rood, J. J., van, Trnka, Z., and Walford, R. L.: 1984, p.4–8, Histocompatibility Testing, Springer-Verlag, Berlin., Tiercy, J.-M., Gorski, J., Betuel, H., Freidel, A. C., Gebuhrer, L., Jeannet; H., and Mach, B.: 1989, 24; p.1–14, Hum Immunol., Gorski, 1989: 24; p145–149, 1. J. Hum Immunol., Kao, H. T., Gregersen, P. K., Tang, J. C., Takahashi, T., Wang, C. Y., and Silver, 1.: 1989, 142; p.1743, J Immunol). The nucleotide sequence reported by these investigators(see supra) is also incorporated in FIG. 1. The dashed line indicates the same nucleotide sequences as those illustrated at the top of FIG. 1. The nucleotide sequences of the oligonucleotide probes are indicated by arrows: The nucleotide sequence indicated by a right-pointed arrow encodes amino acids. The nucleotide sequence indicated by a left-pointed arrow does not encode amino acid. An amino acids sequence in the first domain in the DRβ1 chain of DRB1-14c differs from that of DRB1*1401 at amino acid numbers, 16, 57, and 60. Glutamine (amino acid number 16) is unique to DRB1-14c and not found in other DR types. Differences between DRB1*1401 and DRB1-14c are found in amino acid numbers 57 and 60, corresponding to the oligonucleotide probe F143. On the other hand, DRB1*1402 and DRB1-14c differ from each other at six amino acid positions, 16, 28, 37, 70, 74, and 86. The nucleotide sequence encoding glutamic acid (amino acid number 28) is found in the sequence of F52c. The nucleotide sequence encoding glutamine and alanine (amino acid numbers 70, 74) is found in the sequence of F46.

Genetic Typing of DR Antigens Using Oligonucleotide Probes Synthesized According to Nucleotide Sequence of DRB1-14c DRB1-14c specific oligonucleotide probes, F144 and F142, were synthesized. Glutamine (amino acid number 16) encoded by DRB1-14c was found to be encoded in the sequence of F144. The oligonucleotide F 142 contains thymine (nucleotide number 174) which is uniquely found in DRB1-14c and results in a silent alteration of the amino acid sequence. F142 also contains the nucleotide sequence corresponding to asparagine (amino acid number 57) and tyrosine (amino acid number 60) which are found in many other DRB1 genes including DRB1*1402, DRB1*1301, DRB1*1302 and DRB1-JX 6 and other DRB1 genes.

FIG. 2 shows genetic typing of DR antigen genes at the DNA level using the oligonucleotide probes according to a dot blotting method. The ordinate represents donors and serologically classified DR antigens and the abscissa represents oligonucleotide probes. A dot indicates hybridization of the oligonucleotide probe to the DNA of a donor.

Blood of Japanese volunteers and established B cell lines obtained from The Tenth International HLA Workshop (Yang, S. Y., Milfold, E., Hammerling, U., and Dupont, B.: 1987, 2; No. 1,p.7, Tenth International Histocompatibility Workshop Newsletter, New York, Central Science Office of Histocompability Workshop) were used as samples to investigate genetic polymorphism.

Chromosomal DNA was prepared according to a method known in the art. 1 ug of the chromosomal DNA was amplified with 30 cycles of PCR using primers, GH46 and DRβAMP1. The amplified 288bp DNA fragment was denatured by 0.2N NaOH at room temperature for 10 minutes. Then, ammonium acetate was added to the denaturing mixture to a final concentration of 1M. The solution was immediately spotted on a Hybond-N, nylon membrane, then the membrane was air-dried and baked at 80° C. for 2 hours. The membrane was placed in solution containing 6× SSC, 0.5% SDS, 5× Denhardt's solution (1× Denhardt 's solution: 0.02% bovine serum albumin, 0.02% ficol, 0.02% polyvinylpyrolidone), 20 ug/ml of heat denatured herring sperm DNA and incubated at 37° C for 30 minutes. $^{32}$P-labelled oligonucleotide probes were added to the mixture to a final concentration of 1 ng/ml and the mixture was incubated at 37° C. for 3 hours. After hybridization, the membrane was transferred into a solution containing 6× SSC, 0.1% SDS and incubated at room temperature for 5 minutes. The membrane was then washed in a washing solution for 15 minutes at the temperature indicated in Table 1, air-dried, and autoradiographed for more than three hours.

F 142 and F144 (DRB1-14c specific), and F6b, F141, F143, F46, and F52c (nonspecific to DRB1-14c) were hybridized to the DNA on the membrane. FIG. 2 and Table 3 demonstrate that DNA of serologically DRw 14 typed Japanese volunteers such as 36M, 38M, 82F, 26F, MS, GOT hybridized to F142, F144, F6b, and F 141 while DNA with genotypes DRB1*1401 and DRB1*1402 such as 7M, IIT, KW, 24F, 59M, 75M, 57F did not hybridize to F142 and F144. The results suggests that DR1-14c can be distinguished from other DRw14.

Tailing and Immobilization of Oligonucleotide Probes

Oligonucelotide probes except F144 were treated as follows.

200 pmol oligonucleotide probe, 4 ul of 100 mM dTTP, 10 ul of 10× tailing buffer (1M sodium cacodylate/pH 7.6, 250 mM Tris-HCl/pH 7.6, 2 mM dithiothreitol) were combined. 10 ul of 10 mM COCl$_2$ and 25 unit/ul of terminal deoxiribonucleotide transferase were added to the mixture in this order to bring the final volume 100 ul. The mixture was incubated at 37° C. for 1.5 hours and extracted 2× with 100 ul of a phenol/chroloform (1:1) solution. 10 ul of 3M sodium acetate and 330 ul of ethanol were added to the extract, mixed, and incubated at -20° C for 30 minutes. After incubation, the mixture was centrifuged and the pellet was washed with 70% ethanol and dried under vacuum. The pellet was then dissolved in 50 ul of water, 42 ul of which was heated at 65° C for 5 minutes and cooled on an ice. 1158 ul of 10× SSC was added to the solution and mixed. The solution (200 ul each) was blotted onto a nylon membrane using Milliblot-D (Millipore) and the well was washed with 10× SSC. Stratalinker was added to the well and the membrane was exposed to UV-light (120,000 uJ). The membrane was then washed in a solution containing 5× SSC, 0.5% SDS at 37° C. for 15 minutes and in water 5 minutes, and air-dried at room temperature.

Biotinilation of DRB Gene Fragment Using PCR 5 ul of 10× PCR buffer(200 mM Tris-HCl, 15 mM MgCl, 250 mM KCl, 0.5% Tween 20, 100 ug/ml of BSA), 1 ul of each of 2.5 mM dATP, 2.5 mM dCTP, 2.5 mM dGTP, 1 ul of 1.5 mM dTTP, 1.25 ul of 0.5 mM Bio-21-dUTP, 1 ul of 10 uM primer (FPR 1 and DRβAMP1[1:1(mole/mole)] and 1 ug of DNA were combined. Water was added to the mixture to bring it to 49 ul. The mixture was vortexed, heated at 95° C. for 5 minutes and cooled at room temperature. 1 ul of Taq I DNA polymerase (2.5 unit/ul) was added to the mixture and 40 ul of mineral oil was layered on it. The DNA was amplified by 30 cycles of PCR (1st cycle: at 55° C. for 2 minutes, at 72° C. for 3 minutes, 2–291 h cycle: at 94° C. for 50 seconds, at 55° C. for 1 minute, at 72° C for 2 minutes, 30th cycle: at 72° C. for 3 minutes) using Astec PC-500. After amplification, 1 ul of glycogen (10 mg/ul), 5 ul of 3M sodium acetate/pH5.5, and 165 ul of ethanol were added to 50 ul of the mixture. The mixture was vortexed and incubated at −20° C. for 30 minutes. The mixture was centrifuged at 12,000 rpm for 5 minutes. The pellet was washed with 70% ethanol, dried under vaccum and dissolved in 108 ul of water (concentration of DNA: 0.01 ug/ul). 8 ul of the DNA solution was electrophoresed through 1.0% agarose gel to determine the size of the DNA.

Hybridization

The probe immobilized on the membrane was placed in a plastic bag. 2 ml of hybridization buffer (50 mM Tris-HCl/pH. 8.0, 3M tetramethyl ammonium chloride, 2 mM EDTA/pH 8.0, 5× Denhardt's solution 0.1% SDS, 100 ug of denatured DNA) was added to the bag. The bag was incubated at 42° C. for 50 minutes and then 100 ul of Amplified DNA (100 ng) was added to the bag. The bag was further incubated with shaking at 42° C. for 12 hours. After hybridization, the membrane was removed from the bag and washed 2× with a washing solution I (2× SSPE, 0.1% SDS) at room temperature at 5 minute interval, once with a washing solution II (50 mM Tris-HCl/pH 8.0, 3M tetramethyl ammonium chloride 2 mM EDTA, 5× Denhardt's, 0.1% SDS) at room temperature for 5 minutes, once with a washing solution II at 58° C. for 20 minutes, and once with 2× SSC at room temperature for 5 minutes.

Detection

In this detection step, PhotoGene™Nucleic Detection System was used.

The membrane was washed in TBS-Tween 20 (100 mM Tris-HCl, 150 mM NaCl, 0.05% Tween 20) at room temperature for 1 minute, placed in a blocking solution Containing 3% BSA and TBS-Tween 20 (0.75 ml per 1 cm² of the membrane) and incubated at room temperature for 50 minutes. The membrane was then placed in a solution containing Streptavidin conjuguted alkaline phosphatase diluted with TBS-Tween 20 (1: 3000) and incubated at room temperature for 10 minutes. The membrane was washed 2× with a TBS-Tween 20 solution (1 ml per 1 cm² of the membrane) at room temperature at 15 minute intervals and once with a 10-fold diluted TBS-Tween 20 solution at room temperature for 1 hour. The membrane was removed, place on Whatman 3MM paper to blot the washing solution and put in a holder. A detection reagent was dropped on the membrane and the membrane was covered with the holder. The holder was incubated for 2 hours and then X-ray film or Hyper film (Amersham) was overlayed on the membrane and exposed for 5 minutes. The film was developed and the results are shown in FIG. 2.

What is claimed is:
1. A method of genetic typing which comprises the steps of (1) hybridizing denatured and immobilized test DNA with a DNA probe labelled with a substance selected from the group consisting of radioisotope, fluorescent substance, color former, and luminescent substance, said DNA probe being selected from the group consisting of the sequence described in SEQ ID NO. 3 and the sequence described in SEQ ID NO. 4, and (2) detecting the labelled DNA hybridized to immobilized test DNA by x-ray film exposure, fluorescence, photometry or luminescence; and (3) correlating detected DNA from step (2) with a specific human leukocyte antigen DR.

2. A DNA molecule consisting of the nucleotide sequence as described in SEQ ID NO:2.

3. An isolated DNA molecule of human leukocyte antigen DRB1-14c, having the nucleotide sequence as described in SEQ ID NO:2.

4. A DNA probe consisting of the nucleotide sequence as described in SEQ ID NO:3.

5. A DNA probe specific for genetic typing of human leukocyte antigen DRB1-14c at the DNA level, comprising the nucleotide sequence as described in SEQ ID NO:3.

6. The DNA probe of claim 4 or claim 5 which is labelled with a radioisotope, fluorescent substance, color former or luminescent substance.

7. The DNA probe of claim 4 or claim 5 which is immobilized on a membrane.

8. A DNA probe consisting of the nucleotide sequence as described in SEQ ID NO:4.

9. A DNA probe specific for genetic typing of human leukocyte antigen DRB1-14c at the DNA level, comprising the nucleotide sequence as described in SEQ ID NO:4.

10. The DNA probe of claim 8 or claim 9 which is labelled with a radioisotope, fluorescent substance, color former or luminescent substance.

11. The DNA probe of claim 8 or claim 9 which is immobilized on a membrane.

* * * * *

SEQUENCE LISTING ( 1 ) GENERAL INFORMATION:

( i i i ) NUMBER OF SEQUENCES:12

( 2 ) INFORMATION FOR SEQ ID NO: 1:

( i ) SEQUENCE CHARACTERISTICS:
        ( A ) LENGTH:80 amino acids
        ( B ) TYPE:amino acid
        ( C ) TOPOLOGY:linear     ( i i ) MOLECULE TYPE:Protein     ( i i i ) HYPOTHETICAL:no     ( v i ) ORIGINAL SOURCE:
        ( A ) ORGANISM:human
        ( H ) CELL TYPE:blood     ( i x ) FEATURE:
        ( A ) NAME/KEY:HLA-DRW/4C
        ( B ) LOCATION:amino acids 7 to 86
        ( C ) IDENTIFICATION METHOD:similarity to other DRB1 sequences
        ( D ) OTHER INFORMATION:deduced from nucleotide sequence     ( x ) PUBLICATION INFORMATION:
        ( A ) AUTHORS:Obata, Fumiya
            Ito, Ichiro
            Abe, Akio
            Ohkubo, Midori
            Onda, Keiji
            Yang, Yong- guang
            Watanabe, Koji
            Kahiwagi, Noboru
        ( B ) TITLE:Sequence Analysis and HLA- DR Genotyping of a Novel HLA-DRw14 Allele
        ( C ) JOURNAL:Immunogenetics
        ( D ) VOLUME:32
        ( E ) ISSUE:1
        ( F ) PAGES:313-320
        ( G ) DATE:1990
        ( K ) RELEVANT RESIDUES IN SEQ ID NO: 1: AMINO ACIDS FROM 8 TO 8

( x i ) SEQUENCE DESCRIPTION:SEQ ID NO: 1:

```
Phe  Leu  Glu  Tyr  Ser  Thr  Ser  Glu  Cys  Gln  Phe  Phe  Asn  Gly  Thr  Glu  Arg
 1              5                        10                      15

Val  Arg  Phe  Leu  Asp  Arg  Tyr  Phe  His  Asn  Gln  Glu  Glu  Phe  Val  Arg  Phe
          20                  25                      30

Asp  Ser  Asp  Val  Gly  Glu  Tyr  Arg  Ala  Val  Thr  Glu  Leu  Gly  Arg  Pro  Asp
 35                      40                  45                          50

Ala  Glu  Tyr  Trp  Asn  Ser  Gln  Lys  Asp  Leu  Leu  Glu  Arg  Arg  Arg  Ala  Glu
               55                  60                      65

Val  Asp  Thr  Tyr  Cys  Arg  His  Asn  Tyr  Gly  Val  Val
          70                  75                      80
```

( 2 ) INFORMATION FOR SEQ ID NO: 2:

( i ) SEQUENCE CHARACTERISTICS:
    ( A ) LENGTH:241 base pairs
    ( B ) TYPE:nucleic acid
    ( C ) STRANDEDNESS:double
    ( D ) TOPOLOGY:linear   ( i i ) MOLECULE TYPE:genomic DNA   ( i i i ) HYPOTHETICAL:yes   ( i v ) ANTI-SENSE:no   ( v i ) ORIGINAL SOURCE:
    ( A ) ORGANISM:human
    ( G ) CELL TYPE:blood   ( v i i ) IMMEDIATE SOURCE:
    ( A ) LIBRARY:genomic
    ( B ) CLONE:pDR14C(38M-103F)

( x ) PUBLICATION INFORMATION:
    ( A ) AUTHORS:Obata, Fumiya
      Ito, Ichiro
      Abe, Akio
      Ohkubo, Midori
      Onda, Keiji
      Yang, Yong- guang
      Watanabe, Koji
      Kashiwagi, Noboru
    ( B ) TITLE:Sequence Analysis and HLA- DR Genotyping of a Novel
      HLA-DRw14 Allele
    ( C ) JOURNAL:Immunogenetics
    ( D ) VOLUME:32
    ( E ) ISSUE:1
    ( F ) PAGES:313-320
    ( G ) DATE:1990
    ( K ) RELEVANT RESIDUES IN SEQ ID NO: 2: FROM 19 TO 259

( x i ) SEQUENCE DESCRIPTION:SEQ ID NO: 2:

```
TTTCTTGGAG  TACTCTACGT  CTGAGTGTCA  ATTCTTCAAT  GGGACGGAGC  GGGTGCGGTT   60
CCTGGACAGA  TACTTCCATA  ACCAGGAGGA  GTTCGTGCGC  TTCGACAGCG  ACGTGGGGGA  120
GTACCGGGCG  GTGACGGAGC  TGGGGCGGCC  TGATGCTGAG  TACTGGAACA  GCCAGAAGGA  180
CCTCCTGGAG  CGGAGGCGGG  CCGAGGTGGA  CACCTATTGC  AGACACAACT  ACGGGGTTGT  240
G                                                                      241
```

( 2 ) INFORMATION FOR SEQ ID NO: 3:

( i ) SEQUENCE CHARACTERISTICS:
    ( A ) LENGTH:19 bases
    ( B ) TYPE:nucleic acid
    ( C ) STRANDEDNESS:single
    ( D ) TOPOLOGY:linear   ( i i ) MOLECULE TYPE:oligonucleotide DNA   ( i i i ) HYPOTHETICAL:yes   ( i v ) ANTI-SENSE:no   ( v i ) ORIGINAL SOURCE:
    ( A ) ORGANISM:human
    ( G ) CELL TYPE:blood   ( v i i ) IMMEDIATE SOURCE:
    ( A ) LIBRARY:chemically synthesized   ( x ) PUBLICATION INFORMATION:
    ( A ) AUTHORS:Obata, Fumiya
      Ito, Ichiro
      Abe, Akio
      Ohkubo, Midori
      Onda, Keiji Yang, Yong- guang
Watanabe, Koji
Kashiwagi, Noboru
(B) TITLE:Sequence Analysis and HLA- DR Genotyping of a Novel
HLA-Drw14 Allele
(C) JOURNAL:Immunogenetics
(D) VOLUME:32
(E) ISSUE:1
(F) PAGES:313-320
(G) DATE:1990
(K) RELEVANT RESIDUES IN SEQ ID NO: 3: FROM 1 TO 19

(x i) SEQUENCE DESCRIPTION:SEQ ID NO: 3:

AGTGTCAATT CTTGAATGG    19

(2) INFORMATION FOR SEQ ID NO: 4:

(i) SEQUENCE CHARACTERISTICS:
(A) LENGTH:19 bases
(B) TYPE:nucleic acid
(C) STRANDEDNESS:single
(D) TOPOLOGY:linear (i i) MOLECULE TYPE:oligonucleotide DNA (i i i) HYPOTHETICAL:yes (i v) ANTI-SENSE:yes (v i) ORIGINAL SOURCE:
(A) ORGANISM:human
(G) CELL TYPE:blood (v i i) IMMEDIATE SOURCE:
(A) LIBRARY:chemically synthesized (x) PUBLICATION INFORMATION:
(A) AUTHORS:Obata, Fumiya
Ito, Ichiro
Abe, Akio
Ohkubo, Midori
Onda, Keiji
Yang, Yong- guang
Watanabe, Koji
Kashiwagi, Noboru
(B) TITLE:Sequence Analysis and HLA- DR Genotyping of a Novel
HLA-DRw14 Allele
(C) JOURNAL:Immunogenetics
(D) VOLUME:32
(E) ISSUE:1
(F) PAGES:313-320
(G) DATE:1990
(K) RELEVANT RESIDUES IN SEQ ID NO: 4: FROM 1 TO 19

(i x) SEQUENCE DESCRIPTION:SEQ ID NO: 4:

AGTACTCAGC ATCAGGCCG    19

(2) INFORMATION FOR SEQ ID NO: 5:

(i) SEQUENCE CHARACTERISTICS:
(A) LENGTH:25 bases
(B) TYPE:nucleic acid
(C) STRANDEDNESS:single
(D) TOPOLOGY:linear (i i) MOLECULE TYPE:oligo nucleotide DNA (i i i) HYPOTHETICAL:yes (i v) ANTI-SENSE:no (v i) ORIGINAL SOURCE:
(A) ORGANISM:human (v i i) IMMEDIATE SOURCE:
(A) LIBRARY:chemically synthesized ( i x ) FEATURE:
    ( A ) NAME/KEY:DRB-14c primer
    ( B ) LOCATION:nucleotides 42-65
    ( C ) IDENTIFICATION METHOD:hybridization
    ( D ) OTHER INFORMATION:nucleic acid position 17(N) is C or T ( x ) PUBLICATION INFORMATION:
    ( A ) AUTHORS:Obata, Fumiya
        Ito, Ichiro
        Kaneko, T.
        Ohkubo, M.
        Ishimoto, A.L.
        Abe, Akio
        Kashiwagi, Noboru
    ( B ) TITLE:Oligonucleotide Genotyping as a Method of Detecting
        the HLA- DR2(DRw15)-Dw2,-DR2(DRw15)-Dw12,-DR4-Dw15,
        - DR4- D"KT2"Haplotypes in the Japanese Population
    ( C ) JOURNAL:Tissue Antigens
    ( D ) VOLUME:33
    ( E ) ISSUE:1
    ( F ) PAGES:550-558
    ( G ) DATE:---
    ( K ) RELEVANT RESIDUES IN SEQ ID NO: 5: FROM 1 TO 25

( x i ) SEQUENCE DESCRIPTION:SEQ ID NO: 5:

AGTGTCAATT CTTGAATGGG ACGGA    25

( 2 ) INFORMATION FOR SEQ ID NO: 6:

( i ) SEQUENCE CHARACTERISTICS:
        ( A ) LENGTH:20 bases
        ( B ) TYPE:nucleic acid
        ( C ) STRANDEDNESS:single
        ( D ) TOPOLOGY:linear     ( i i ) MOLECULE TYPE:oligonucleotide DNA     ( i i i ) HYPOTHETICAL:yes     ( i v ) ANTI-SENSE:yes     ( v i ) ORIGINAL SOURCE:
        ( A ) ORGANISM:human     ( v i i ) IMMEDIATE SOURCE:
        ( A ) LIBRARY:chemically synthesized     ( x ) PUBLICATION INFORMATION:
        ( A ) AUTHORS:Todd, J.A.
            Bell, J.I.
            McDevitt, H.O.
        ( B ) TITLE:HLA-DQ Gene Contributes to Susceptibility and
            Resistance to Insulin-Dependent Diabetes mellitus.
        ( C ) JOURNAL:Nature
        ( D ) VOLUME:329
        ( E ) ISSUE:1
        ( F ) PAGES:599-604
        ( G ) DATE:1987
        ( K ) RELEVANT RESIDUES IN SEQ ID NO: 6: FROM 1 TO 19

( i x ) SEQUENCE DESCRIPTION:SEQ ID NO: 6:

CGCTGCACTG TGAAGCTCTC    20

( 2 ) INFORMATION FOR SEQ ID NO: 7:

( i ) SEQUENCE CHARACTERISTICS:
        ( A ) LENGTH:27 bases
        ( B ) TYPE:nucleic acid
        ( C ) STRANDEDNESS:single
        ( D ) TOPOLOGY:linear     ( i i ) MOLECULE TYPE:oligonucleotide DNA     ( i i i ) HYPOTHETICAL:yes ( i v ) ANTI-SENSE:no ( v i ) ORIGINAL SOURCE:
    ( A ) ORGANISM:human ( v i i ) IMMEDIATE SOURCE:
    ( A ) LIBRARY:chemically synthesized ( x ) PUBLICATION INFORMATION:
    ( A ) AUTHORS:Scharf, S.J.
        Long, C.M.
        Erlich, H.A.
    ( B ) TITLE:Sequence Analysis of the HLA-DR and HLA-DQ Loci
        from Three Pemphigus vulgaris Patients
    ( C ) JOURNAL:Hum. Immunol.
    ( D ) VOLUME:22
    ( E ) ISSUE:1
    ( F ) PAGES:61-69
    ( G ) DATE:1988
    ( K ) RELEVANT RESIDUES IN SEQ ID NO: 7: FROM 1 TO 27

( x i ) SEQUENCE DESCRIPTION:SEQ ID NO: 7:

CCGGATCCTT CGTGTCCCCA CAGCACG    27

( 2 ) INFORMATION FOR SEQ ID NO: 8:

( i ) SEQUENCE CHARACTERISTICS:
        ( A ) LENGTH:19 bases
        ( B ) TYPE:nucleic acid
        ( C ) STRANDEDNESS:single
        ( D ) TOPOLOGY:linear     ( i i ) MOLECULE TYPE:oligonucleotide DNA     ( i i i ) HYPOTHETICAL:yes     ( i v ) ANTI-SENSE:no     ( v i ) ORIGINAL SOURCE:
        ( A ) ORGANISM:human     ( v i i ) IMMEDIATE SOURCE:
        ( A ) LIBRARY:chemically synthesized     ( x ) PUBLICATION INFORMATION:
        ( A ) AUTHORS:Tiercy, J.-M.
            Gorski, J.
            Betuel, H.
            Freidel, A.C.
            Gebuhrer, L.
            Jeannet, M.
            Mach, B.
        ( B ) TITLE:DNA Typing of DRw6 Subtypes:Correlation with DRB1
            and DRB3 Allelic Sequences by Hybridization with
            Oligonucleotide Probes.
        ( C ) JOURNAL:Hum. Immunol.
        ( D ) VOLUME:24
        ( E ) ISSUE:1
        ( F ) PAGES:1-14
        ( G ) DATE:1989
        ( K ) RELEVANT RESIDUES IN SEQ ID NO: 8: FROM 1 TO 19

( x i ) SEQUENCE DESCRIPTION:SEQ ID NO: 8:

TGCTGCGGAG CACTGGAAC    19

( 2 ) INFORMATION FOR SEQ ID NO: 9:

( i ) SEQUENCE CHARACTERISTICS:
        ( A ) LENGTH:19 bases
        ( B ) TYPE:nucleic acid
        ( C ) STRANDEDNESS:single
        ( D ) TOPOLOGY:linear     ( i i ) MOLECULE TYPE:oligonucleotide DNA     ( i i i ) HYPOTHETICAL:yes (iv) ANTI-SENSE:no (vi) ORIGINAL SOURCE:
    (A) ORGANISM:human (vii) IMMEDIATE SOURCE:
    (A) LIBRARY:chemically synthesized (x) PUBLICATION INFORMATION:
    (A) AUTHORS:Abe, A.
        Ito, I.
        Ohkubo, M.
        Kaneko, T.
        Ito, K.
        Kato, H.
        Kashiwagi, N.
        Obata, F.
    (B) TITLE:Two Distinct Subtypes of the HLA-DRw12 Haplotypes
        in the Japanese Population Detected by Nucleotide
        Sequence Analysis and Oligonucleotide Genotyping
    (C) JOURNAL:Immunogenetics
    (D) VOLUME:30
    (E) ISSUE:1
    (F) PAGES:422-426
    (G) DATE:1989
    (K) RELEVANT RESIDUES IN SEQ ID NO: 9: FROM 1 TO 19

(xi) SEQUENCE DESCRIPTION:SEQ ID NO: 9:

GTGTCTGCAA TAGGTGTCC        19

(2) INFORMATION FOR SEQ ID NO: 10:

(i) SEQUENCE CHARACTERISTICS:
        (A) LENGTH:18 bases
        (B) TYPE:nucleic acid
        (C) STRANDEDNESS: single
        (D) TOPOLOGY:linear (ii) MOLECULE TYPE:oligonucleotide DNA (iii) HYPOTHETICAL:yes (iv) ANTI-SENSE:no (vi) ORIGINAL SOURCE:
        (A) ORGANISM:human (vii) IMMEDIATE SOURCE:
        (A) LIBRARY:chemically synthesized (x) PUBLICATION INFORMATION:
        (A) AUTHORS:Scharf, S.J.
            Friedman, A.
            Brautbar, C.
            Szafer, F.
            Steiman, L.
            Horn, G.
            Gyllensten, U.
            Erlich, H.A.
        (B) TITLE:HLA Class II Allelic Variation and Susceptibility to
            Pemphigus vulgaris
        (C) JOURNAL:Proc. Natl. Acad. Sci. USA
        (D) VOLUME:85
        (E) ISSUE:1
        (F) PAGES:3504-3508
        (G) DATE:1988
        (K) RELEVANT RESIDUES IN SEQ ID NO: 10: FROM 1 TO 18

(ix) SEQUENCE DESCRIPTION:SEQ ID NO: 10:

GCAGAGGCGG GCCGCGGT        18

(2) INFORMATION FOR SEQ ID NO: 11:

(i) SEQUENCE CHARACTERISTICS:
        (A) LENGTH:19 bases (B) TYPE: nucleic acid
(C) STRANDEDNESS: single
(D) TOPOLOGY: linear (i i) MOLECULE TYPE: oligonucleotide DNA (i i i) HYPOTHETICAL: yes (i v) ANTI-SENSE: yes (v i) ORIGINAL SOURCE:
(A) ORGANISM: human (v i i) IMMEDIATE SOURCE:
(A) LIBRARY: chemically synthesized (x) PUBLICATION INFORMATION:
(A) AUTHORS: Tiercy, J.-M.
Gorski, J.
Betuel, H.
Friedel, A.C.
Gebuhrer, L.
Jeannet, M.
Mach, B.
(B) TITLE: Typing of DRw6 Subtypes: Correlation with DRB1 and DR Allelic Sequences by Hybridization with Oligonucleotide P
(C) JOURNAL: Hum. Immunol.
(D) VOLUME: 24
(E) ISSUE: 1
(F) PAGES: 1-14
(G) DATE: 1989
(K) RELEVANT RESIDUES IN SEQ ID NO: 11: FROM 1 TO 18

AGCGCACGAA CTCCTCCTG 19

(2) INFORMATION FOR SEQ ID NO: 12:

(i) SEQUENCE CHARACTERISTICS:
(A) LENGTH: 19 bases
(B) TYPE: nucleic acid
(C) STRANDEDNESS: single
(D) TOPOLOGY: linear (i i) MOLECULE TYPE: oligonucleotide DNA (i i i) HYPOTHETICAL: yes (v i) ORIGINAL SOURCE:
(A) ORGANISM: human (v i i) IMMEDIATE SOURCE:
(A) LIBRARY: chemically synthesized (x) PUBLICATION INFORMATION:
(A) AUTHORS: Tiercy, J.-M.
Gorski, J.
Jeannet, M.
Mach, B.
(B) TITLE: Identification and Distribution of Three Serologically Undetected Alleles of HLA-DR by Oligonucleotide DNA Typing Analysis.
(C) JOURNAL: Proc. Natl. Acad. Sci. USA
(D) VOLUME: 85
(E) ISSUE: 1
(F) PAGES: 198-202
(G) DATE: 1988
(K) RELEVANT RESIDUES IN SEQ ID NO: 12: FROM 1 TO 19

(x i) SEQUENCE DESCRIPTION: SEQ ID NO: 12:

GTTCCTGGAG AGATACTTC 19